(12) United States Patent
Buonamici

(10) Patent No.: US 9,167,842 B2
(45) Date of Patent: Oct. 27, 2015

(54) FUNCTIONAL FOOD PREPARATION AND USE THEREOF

(76) Inventor: Guglielmo Buonamici, Gello di San Giuliano Terme (IT)

( * ) Notice: Subject to any disclaimer, the term of this patent is extended or adjusted under 35 U.S.C. 154(b) by 0 days.

(21) Appl. No.: 13/993,986

(22) PCT Filed: Dec. 15, 2011

(86) PCT No.: PCT/IB2011/055716
§ 371 (c)(1),
(2), (4) Date: Jun. 13, 2013

(87) PCT Pub. No.: WO2012/080982
PCT Pub. Date: Jun. 21, 2012

(65) Prior Publication Data
US 2013/0280227 A1    Oct. 24, 2013

(30) Foreign Application Priority Data
Dec. 16, 2010    (IT) ................. P12010A0137

(51) Int. Cl.
| | | |
|---|---|---|
| *A61K 31/122* | (2006.01) | |
| *A61K 38/43* | (2006.01) | |
| *A61K 8/37* | (2006.01) | |
| *A23L 1/30* | (2006.01) | |
| *A23C 9/13* | (2006.01) | |
| *A23C 9/152* | (2006.01) | |
| *A23C 11/10* | (2006.01) | |
| *A23L 2/52* | (2006.01) | |
| *A61K 31/045* | (2006.01) | |
| *A61K 31/352* | (2006.01) | |
| *A61K 31/365* | (2006.01) | |
| *A61K 36/062* | (2006.01) | |
| *A61K 36/48* | (2006.01) | |
| *A61K 45/06* | (2006.01) | |
| *A61K 31/519* | (2006.01) | |
| *A61K 31/714* | (2006.01) | |

(52) U.S. Cl.
CPC ............... *A23L 1/3002* (2013.01); *A23C 9/13* (2013.01); *A23C 9/152* (2013.01); *A23C 11/10* (2013.01); *A23C 11/103* (2013.01); *A23L 1/30* (2013.01); *A23L 2/52* (2013.01); *A61K 31/045* (2013.01); *A61K 31/122* (2013.01); *A61K 31/352* (2013.01); *A61K 31/365* (2013.01); *A61K 31/519* (2013.01); *A61K 31/714* (2013.01); *A61K 36/062* (2013.01); *A61K 36/48* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,391,308 B1 * | 5/2002 | Empie et al. ................ 424/757 |
| 2010/0239603 A1 * | 9/2010 | Wang et al. ............. 424/195.16 |
| 2012/0121758 A1 * | 5/2012 | Becker ........................... 426/18 |
| 2013/0071372 A1 * | 3/2013 | Naidu et al. ................ 424/94.4 |

FOREIGN PATENT DOCUMENTS

WO    WO 2006016357 A1 *    2/2006

OTHER PUBLICATIONS

Nijjar, P.S., Burke, F.M., Bloesch, A., and Rader, D.J. "Role of dietary supplements in lowering low-density lipoprotein cholesterol: A review", Journal of Clinical Lipidology, Epub. Jul. 2010, vol. 4, pp. 248-258.*
Zhu, X., Zhang, H., and Lo, R. "Phenolic Compounds from the Leaf Extract of Artichoke (*Cynara scolymus* L.) and Their Antimicrobial Activities", Journal of Agricultural and Food Chemistry 2004, vol. 52, pp. 7272-7278.*
Bora, K.S. and Sharma, A. "Phytochemical and pharmacological potential of Medicago sativa: A review", Pharmaceutical Biology, Epub. Oct. 2010, vol. 49, pp. 211-220.*
Jager, A.K., Saaby, L., Kudsk, D.S., Witt, K.C., and Molgaard, P. "Short communication: Influence of pasteurization on the active compounds in medicinal plants to be used in dairy products", Journal of Dairy Science, Epub. Jun. 2010, vol. 93, pp. 2351-2353.*
Leifert, W.R., and Abeywardena, M.H. "Cardioprotective actions of grape polyphenols", Nutrition Research 2008, vol. 28, pp. 729-737.*

* cited by examiner

*Primary Examiner* — Renee Claytor
*Assistant Examiner* — Michelle F Paguio Frising
(74) *Attorney, Agent, or Firm* — R. Ruschena Patent Agent, LLC

(57) ABSTRACT

The invention concerns a functional food preparation based on milk/dairy products added with botanical products containing various active principles. The milk/dairy products, which can be obtained from fresh or pasteurized animal milk, soy milk or rice milk, comprise *Saccharum officinarum* containing polycosanols, *Monascus purpureus* containing plant statins, and *Glycine max* containing isoflavones and coenzymes. Further components can be added to the preparation to improve its organoleptic properties. The invention also refers to the use of the preparation as a food with functional features which are useful to stabilize the cholesterol and triglycerides amount, having an antioxidant action and protective of arteries and the cardiocirculatory system.

12 Claims, No Drawings

FUNCTIONAL FOOD PREPARATION AND USE THEREOF

CROSS-REFERENCE TO RELATED APPLICATION

The instant application is a national phase of PCT International Patent Application No. PCT/IB2011/055716 filed Dec. 15, 2011, pending, which claims priority to Italian Patent Application No. PI2010A000137 filed Dec. 16, 2010, pending, the entire specifications of both of which are expressly incorporated herein by reference.

The present invention concerns a food preparation comprising botanical products which contain various active principles suitable for preventing and treating disorders, in particular hypercholesterolemia and cardio-circulatory disorders.

The main feature of the functional food preparation of the invention is that it combines a specific phytoestrogen, that is soy isoflavone, with specific active principles, that is polycosanols and coenzymes, in a single widely used food preparation belonging to the category of dairy products and/or soy based preparations and/or rice based preparations.

Isoflavones are chemical compounds present in nature belonging to the category of botanical phenols comprised in the class of flavonoids. Isoflavones can be found in Leguminoseae and Iridaceae and in particular the can be found in Papilionideae, which are of the family of Leguminoseae, so that they can be found in foods such as chickpeas, grains, beans, fennels, lentils, soybeans.

Several clinical studies (Zhuo X G et al. 2004; G. Moscow, 2008; S. Zhan et al. 2005) have highlighted the effects of soy protein and of the isoflavones contained in them on cholesterol and triglycerides and and they have shown that soy protein containing isoflavones exerted a significant action to reduce total cholesterol, LDL cholesterol (low density lipoprotein) and triglycerides, with an action of increasing HDL cholesterol (high density lipoprotein—good cholesterol). The reducing effect has been shown to be as greater as higher was the cholesterol level before treatment.

Isoflavones, in structural and functional terms, are similar to estrogens produced by the body, with the property of binding to the same receptors. For this reason they are commonly called phytoestrogens, including one of the most important and studied which is the genistein and the respective b-glucoside genistein. In the soy-based foods they can be found in the form glucosinolate, although the bio-active form is the glucose free isoflavone, which is the aglycone. Therefore, natural soy isoflavones must be activated, through the hydrolysis of the glucosidic group, to acquire their biological function.

In the gastrointestinal apparatus are present enzymes called beta-glucosidase involved in the separation of glucose so transforming the molecule of glucose into the active form named aglycone, and in this form it can be absorbed in the intestine.

The aglycone is structurally similar to estrogen and can bind to the same receptors. In humans, there are two different receptors for estrogen and called ERb (A. Bitto, 2010). With regards to such receptors there is a different and very interesting receptor binding activity made by phytoestrogens, especially genistein, because genistein has a high affinity for ERb estrogen-like, 20 times greater than the affinity for the receptor ERa. This differentiated action of genistein leads to a different profile of safety and efficacy; effectiveness can be explained by referring to the high affinity of genistein for the estrogen receptor type b (ERb) which is abundant in the cardiovascular system.

This publication also showed that the daily intake of genistein aglycone resulted in a statistically significant reduction of both the decrease in plasma cholesterol and in the number and intensity of hot flushes, with absence of side effects, but the interest on isoflavones, further to receiving scientific confirmations on its cholesterol-lowering action, has gone far beyond even coming to confirm the protective action on bone and cardiovascular system.

Several studies (M J Tikkanen & Adlercreutz, H., 2010, M. Valente, 2009) have emphasized that the beneficial effect on the cardiovascular are achieved through the modification of the lipid phenotype with reduction in LDL, triglycerides and platelet aggregation, the increase in HDL, apolipoprotein A and coronary vascular reactivity in general.

Genistein also has proven effective in reducing the growth of blood vessels that feed tumors. This seems to explain the protective effect that soy, according to some studies, have against the development of prostate cancer in humans.

In patent EP 0998206 is claimed a food preparation in the form of a powder mixture, containing isoflavones including soy flour, ground flax seeds which contain more phytoestrogens such as lignans, and fructooligosaccharides, inulin in particular, while in patent applications WO97/32593 and GB 1219584 describe mixtures of food components including even these phytoestrogens—isoflavones and lignans—for the production of biscuits with beneficial health effects as supplements of flour in bread production.

Differently, the inventor has realized as particularly synergistic and effective in the prevention and treatment of various disease states including those noted above, the association of isoflavones with specific active principles, other than phytoestrogens, such as active policosanol, coenzymes, plant statins, cynarin and others as described below.

Main object of the present invention is indeed to propose a food preparation that contains botanical substances that combine and optimize a cholesterol stabilizing action with a protective action of the cardio-vascular.

Further object of the present invention is to propose a food preparation including plant substances that, in addition to optimized properties for stabilizing cholesterol and for cardiovascular protection, they also have an antioxidant, antitumor and liver protection action.

Another object of the present invention is to propose a food preparation with the above characteristics based on dairy foods and/or soybean and/or rice, preferably in liquid or semi-fluid form.

Policosanols are a mixture of phyto-molecules consisting of high molecular weight aliphatic alcohols extracted primarily from *Saccharum officinarum*, but also from other plants, such as *Medicago sativa*. The main molecules are Octacosanol, Tetracosanol and Esacosanol. The octacosanol is contained in the above vegetables, in cotton, and in the waxy layer of leaves of different plants, and is also in a significant amount in wheat germ oil. The policosanol can be produced synthetically but in this case they are not accompanied by other phytochemicals normally present, so that they are less effective than natural ones. In nature, for example, is always accompanied by octacosanol and synergistic with vitamin E and vitamin Group B as well as minerals. The octacosanol extraction process is conducted by cold pressing, without using solvents, which allows to obtain a product rich in vitamin E, a powerful antioxidant factor.

Policosanol also have medicinal properties such as lowering the 'bad' cholesterol (LDL) through the reduction of an enzyme at the base of its production (H. Prat et al., 1999.), and the percentage of triglycerides (Mas R. et al., 1999), as well antiplatelet action on blood (R. Mas et al. 1998; Arruzazabala M L et al. 2002; G. Castano, R. Mas, J C Fernandez et al., 2001) reducing the risk of clogging the blood vessels. The policosanol also have important antioxidant functions and thus are effective in combating free radicals by preventing the oxidation of LDL which may be the root cause of atherosclerotic events.

Numerous clinical studies published up to now (I. Gouna-Berthold et al., 2002) indicate that a dose of policosanol between 10 and 20 mg/day can lower total cholesterol between 17 and 21% and LDL cholesterol between 21 and 29% and raise HDL cholesterol between 8 and 12%; policosanol also reduce triglycerides by 10% on average. Recent studies have confirmed that policosanol is as effective as simvastatin and pravastatin in lowering cholesterol. (Ortensi G., J. Gladstein, H. Valli et al, 1997). Further studies (Castano G. et al, 2003) have shown that the efficacy of policosanol in lowering cholesterol is only slightly less than that of atorvastatin.

This drug, which belongs to the so-called statins, is among the most effective drugs on the market for lowering cholesterol and for the protection of the heart and blood vessels. Statins, chemically speaking, are secondary metabolites of polyketide nature having selective inhibitory action of the enzyme 3-hydroxy-3-methylglutaryl-coenzyme A (HMG-CoA reductase) that catalyzes the reaction of the synthesis of endogenous cholesterol. Depending on the type of interest in their pharmacological activity, processes have been developed for the production of statins by fermentation, using strains of fungi.

The study of the first isolated molecules and used within the drug (lovastatin and mevastatina) made it possible to identify other molecules with greater biological activity and fewer side effects, eg. The provastatina. The study (A. White, 2005) has also extended to the evaluation of the influence of fermentation parameters using strains of *Monascus purpureus* that do not the problems of side effects associated with synthetic statins.

In fact, the ferment of red rice forms after the addition of *Monascus purpureus,* a fungus that grows on the caryopsis of rice, giving him the typical reddish, forming compounds known as monacolins: among them the monacolin K, which is structurally related to lovastatin, one of the most prescribed synthetic statins against cholesterol, and just like this one it has the same pharmacological inhibiting action of KMG-CoA reductase, the enzyme member of the cholesterol biosynthesis in the liver, so making the reduction of plasma cholesterol.

The fermented red rice has long been the subject of detailed studies reported in scientific literature which recognizes to the plant *Oryza sativa* powerful cholesterol reducing properties. In fact, the therapeutic properties of fermented red rice have been known for centuries in traditional Chinese medicine. It is scientifically proven its ability to reduce levels of total cholesterol, LDL—cholesterol and triglycerides.

Isoflavones, policosanol and statins play so everyone, as amply documented in the literature, stabilizing actions against dyslipidemia. However, their action is certainly not identical, and although not yet demonstrable and explicable in terms of bio-molecular process, the inventor has found through experimentation that a balanced intake of the three substances in a single food preparation has stabilizing effect against dyslipldemia which are enhanced compared to those that are the effects of equal amounts of each of these substances taken individually. In addition, each of the three substances has additional health properties and act synergistically together to produce, overall, significant protective effects of the cardio-circulatory, liver protection and antioxidants.

Coenzyme Q10, also known as ubiquinone or vitamin Q, is an organic molecule, and more precisely a benzoquinone with a very long isoprene side chain. This coenzyme, ubiquitous in biological systems, has a similar structure to vitamin K and vitamin E. It is found in abundance in soybeans, grains, nuts and grapes. It participates in redox reactions in organisms. It has a strong scavenging action and therefore protects cell structures from free radicals, and its action is carried out in synergy with vitamin E, in turn protected by coenzyme Q10, which ensures the link with the octacosanol, also linked in turn to vitamins B group and minerals. In fact, this coenzyme is a lipophilic compound insoluble in water having an adjuvant action in electron transport and mitochondrial energy production.

The intake of coenzyme Q10 can exert cardioprotective effects, cytoprotective and neuroprotective; it also carries an action of inhibiting oxidation of LDL cholesterol, which is considered the most pathogenic component of atherosclerosis. (Littaru G P & L. Tiano, 2005; Linnane A W et al. 2002; M. Mizuno et al. 1997; Niklowitz P. et al., 2002).

The coenzyme Q10 exerts an improvement of cellular energy production and synthesis of adenosine triphosphate (ATP). The Q10 conezima thus contributes to the improvement of heart function in people suffering from congestive heart failure and mitochondrial dysfunction and insufficient cellular energy production.

The level of coenzyme Q10 in the human body decreases with age, possibly due to a decrease in its synthesis or because of increased lipid oxidation with age. The coenzyme Q10, for its therapeutic attitudes may be indicated in diseases related to cardiovascular disorders and, in particular, congestive heart failure. It is definitely suited to meet the deficit of CoQ10 caused by intake of inhibitors of HMG-CoA reductase used as cholesterol reducing drugs, such as the above mentioned statins. These can reduce the serum levels of coenzyme Q10 by up to 40%. Recent studies suggest daily Intake of coenzyme Q10 in conjunction with all the treatments that can reduce the natural production.

In view of this it is advantageous the use of this coenzyme in association with policosanol and isoflavones, in place of the association of these active ingredients with green tea catechins (R. Fox, 2008).

The catechins in green tea (*Camellia sinensis*), are polyphenols of the flavan-3-oils belonging to the flavonoid family. The beneficial effects of green tea have long been attributed to the catechin and in particular all'EGCG component (epigallocatechin gallate) ranked as the most powerful antioxidant catechin in green tea. It was tested the ability of catechins to induce increased synthesis of certain phase II liver enzymes, involved in the detoxification of several xenobiotics, and among them also some chemical carcinogens. It was found that EGCG can inhibit the proteolytic enzyme urokinase, an enzyme used by cancer cells to invade healthy tissues and produce metastases. The assignment of antithrombotic effect seems to be attributed to the ability of inhibiting platelet aggregation without affecting coagulation parameters. However it is not clear the mechanism of the possible effect of reducing cholesterol levels. It is assumed, but this has not yet been confirmed by scientific studies, the catechins in green tea can stimulate the secretion of bile salts and fecal excretion of cholesterol.

The cynarin is the extract of *Cynara scolymus* (artichoke) which is derived through crossing varieties and selections from the *Cardo cardunculus* (thistle). It is a herbaceous plant of the family of composite. Its medicinal properties were already known to the Greeks and Egyptians.

This is a plant rich in polyphenols, flavonoids and sterols, it is also rich in polyphenols and organic acids represented by the 5-caffeil chinic acid also known as chlorogenic acid of 1,5-2-caffeil chinic acid.

The artichoke carries out a choleretic action hat is increases coleresys for synergistic action of organic acids and cinaropicrina. It is also linked to this action the lipid-lowering effect: Increase of apollpoprotein A1 and A2 cell receptors by the liver with an increase in HDL. In addition, the artichoke performs an action of inhibiting cholesterol synthesis by inhibition of HMG-CoA reductase.

The beneficial effects of the artichoke stem from its significant content in cynarin which carries cholesterol-lowering action. This thereapeutic effect has been demonstrated by numerous scientific studies. (FINTELMANN V., 1996, R. Gebhardt, 1997; T. Wegener et al., 1999). Therapeutic doses of cynarin vary from 5 g to 50 g. The substances contained in artichoke are absolutely devoid of toxicity.

The main chemical constituents of the artichoke are polyphenols, polyacetals, sterols, acidim organic, mineral salts and aromatic volatile components.

It was pointed out that the cynarin, long considered the key ingredient in artichoke is actually not present in the plant during its complete phenological cycle, but it is formed only during the drying process. From this scientific discovery comes the use in the invention of cynarin obtained from the dried plant.

As mentioned above, the policosanol can be found, in addition to *Saccharum officinarum,* also in *Medicago sativa,* which also contains isoflavones, saponins, coumarins and folic acid. The saponins, glycosides, or saponins, are complex molecules characterized by a aglyconic structure of triterpenic or steroidal nature. They are responsible for the chesteroplasic activity through which total cholesterol and LDL cholesterol are significantly reduced. The coumarins are, in chemical terms, derivatives of 5,6-benzo-2-pirone and can be found in the plant world both in free form and in glycosides, Ie linked as an aglycone to a sugar. Thanks to a certain thrombosis reducing that it has, *Medicago sativa* helps the prevention and treatment of cardiovascular system. Moreover, thanks to its significant content of folic acid, or pteroll (mono) glutamic acid or vitamin B9, it exerts a competitive containment of homocysteine.

Homocysteine is an amino add of great interest for the scientific research for medical risk which may result in an excess of it in our body. In fact the etiology of many human diseases is attributed to it. The term hyperhomocysteinemia indicates an excessive amount of blood homocysteine. Hyperhomocysteinemia is considered an important and independent risk factor predisposing to cardiovascular disease (atherosclerosis, myocardial infarction), cerebrovascular (stroke) and peripheral vascular (arterial and venous thrombosis). It is estimated that persons suffering from hypernomocysteinemia have twice the chance of running into cardio vascular disease compared to those who have values within the normal range. Many studies report that the hyperhomocysteinemia represents a high risk of developing Alzheimer's disease, and it was also observed a high blood level of homocysteine in women with preeclampsia, placental detachment, and miscarriage. High blood levels of homocysteine have also been reported in women who have given birth to underweight children or with neural tube defects. Hyperhomocysteinemia can be considered a predisposing factor for the occurrence of osteoporosis. The vast majority of people with hyperhomocysteinemia follows a diet incorrect and deficient in B vitamins including folic acid.

A diet rich in vegetables brings the right amount of folate. Some researchers argue that hyperhomocysteinemia, is one of the few if not the only condition which can be adequately treated with vitamin supplementation. In fact we know that there are various B vitamins involved in homocysteine metabolism. Several studies confirm that the proper daily intake of B vitamins is able to decrease the plasma levels of homocysteine. Some studies have observed a significant reduction in plasma levels of this amino acid after folic acid intake. It has been shown that a daily folic acid supplement leads to a reduction of about 60% homocysteine, and if the dose doubles, the reduction increases to about 90%.

The folic acids are essential for the synthesis of certain amino acids, for the synthesis of purines and pyrimidines, for the reproduction and growth of cells, particularly of red blood cells. Folic acid participates in nucleic acid synthesis. It is present in milk, potatoes, medical grass, carrots, spinach, green beans, asparagus, wheat germ, yeast, liver, chicken, eggs. Studies have shown that folic acid is a nutrient most often deficient in the diet. Its deficiency leads to increased homocysteine in the blood, leading to a significantly increased risk of ischemic heart disease. According to numerous clinical and academic centers, the introduction of folic acid in the diet results in significant actions to reduce disease with heart disease and stroke. Studies have shown that homocysteine levels decreased by increasing the introduction of folic acid in the diet. A deficiency of vitamin B12 can cause in turn an additional folic acid deficiency which can cause the onset of anemia. Oral contraceptives interfere with the absorption of folic acid. The lipid-lowering drugs, the adamantine, barbiturates, cause a reduction of folic acid in the body. The need for folic acid increases considerably during pregnancy. Studies show that most of the metabolic imbalances or neural tube defects are caused by folic acid deficiency, which can lead to severe deformities in the fetus as a cleft palate, brain damage, spina bifida, slowing growth and learning ability of child. Studies confirm that folic acid should be taken with the diet and that women should take six weeks before conception. Studies show that folic acid deficiency can cause toxemia, premature delivery, postpartum hemorrhage and anemia megaloblastic both to the mother and child. Deficiencies in folic acid, during and after pregnancy, determine the increased risk of cancer or cervical dysplasia. The *Medicago sativa* has a high content of folic acid, which among other things, works by interfering with the decrease of homocysteine in the blood increased as a result of inhibition of the enzyme action HMCoA-reductase determined, in turn, by the action of monacolin K, plant statin of *Monascus purpureus,* developed during fermentation of *Oryza sativa.*

Polyphenols are a family of about 5000 organic molecules widespread in the plant kingdom. They are characterized, as its name indicates, by the presence of multiple phenolic groups associated in more or less complex structures generally of a high molecular weight. In nature, the polyphenols are produced by secondary metabolism of plants, where, in relation to the chemical diversity that characterizes them, cover different roles: defense against herbivores (imparting unpleasant taste) and pathogens (phytoalexins), mechanical support (lignins) and barrier against microbial invasion, attracting pollinators and dispersal of the fruit (anthocyanins), inhibitors of in competition plants growth. From the chemical point of view, the polyphenols are molecules composed of multiple condensed phenolic cycles (organic compounds that possess one or more hydroxyl groups—OH— bound to an aromatic ring). Depending on their structure they can be schematically divided into three different classes: simple phenols, flavonoids, and tannins.

An important, in terms of healthy, polyphenol present in grapes and wine is Resveratrol.

Many in vitro studies have confirmed that the Resveratrol molecule plays an important role in the prevention of human diseases and in maintaining optimal physiological balance essential for leading a peaceful and healthy life.

Mainly, the protective effect of Resveratrol against cardiovascular disease has been demonstrated as well as the action of slowing the evolution of cancer, the fundamental role as antioxidant agent and the action for containing the blood cholesterol. Recently it was discovered a very important action of Resveratrol as an activator of interleukin 10 (IL10) which suggests to the scientific community that it is an activator of immune tolerance and control of allergies.

Another discovery has attributed to Resveratrol the role of deactivator of the NFKappa-B protein, which has a protection of cancer cells by chemotherapy and hinders their destruction. This discovery opens a therapeutic setting of great importance especially in the use of Resveratrol during chemotherapy to protect the body and contribute to more active therapy. Resveratrol can also be used as anti-infective and it was found that in some cases it is useful where some antibiotics are no longer able to function. Finally, Resveratrol has recently been attributed the effect of improving the quality of the skin. Several studies have shown that this substance helps to restore tone and clarity, in addition to significantly counteract the signs of aging. This is due to the combination of its anti-inflammatory and antioxidant. Its vessel relaxing properties results in a significant improvement of blood microcirculation, which involves revitalizing the skin while making it more elastic.

The protective action of Resveratrol on the cardiovascular system is attributed to its antioxidant action and its inhibition of platelet aggregation, which is accomplished through inhibition of the synthesis of eicosanoids and by the action on the metabolism of arachidonic acid. Resveratrol also plays protective action of oxidation of LDL and lipoprotein responsible for transporting cholesterol to the body's cells. Taking Resveratrol exerts an action to reduce levels of total cholesterol and a reduction of fat in the blood. In particular, we found a significant lowering of blood levels of VLDL, which, among the different types of LDL, are those mainly responsible for the onset of atherosclerosis.

Resveratrol has a chemical structure similar to that of diethylstilbestrol, a synthetic estrogen, and this explains its hormone-like activity that allows it to bind and activate estrogen receptors competitively.

Due to its estrogenic effect on cholesterol levels and blood flow, several researchers attribute to Resveratrol the actions of prevention of cardiovascular disease. In addition, promoting the physiological mechanism mediated by nitric oxide, resveratrol is able to induce vessel dilation leading to a lowering of blood pressure. Resveratrol can also play anti-inflammatory activity through inhibition of cyclooxygenase and hydroperoxidases.

The Berberine is a plant alkaloid particularly active in reducing cholesterol. This substance, with its bitter taste and yellow color, is present in the bark, roots and stems, including underground (rhizomes) of plants of the genus *Berberis,* such as barberry (*Berberis vulgaris* L.).

Berberine is also typical of hydraste berberine (*Hydrastis canadensis*) and Huang Lian (*Coptis chinensis*).

For the antisecretory and antimicrobial properties attributed to berberine, the traditional use of berberine addressed the treatment of infections of various kinds, such as bacterial diarrhea and recurrent infections by *Candida albicans.* Recently, there have been documented and reevaluated especially cholesterol-lowering and hypoglycemic properties of berberine. In this sense, the drug has risen to the headlines in 2004, with the study published in Nature Medicine by Kong, Wei J, Abidi et al. (Berberine is a novel cholesterol-Lowering drug working through a unique mechanism distinct from statins). During this research berberine, taken orally by 32 hypercholesterolemic patients for three months, reduced plasma cholesterol by 29%, triglycerides by 35% and LDL cholesterol by 25%. The above data is particularly encouraging, therefore leading to attribute to Berberine properties that make it a possible alternative to statin therapy that can cause side effects. The mechanism by which this drug reduces the plasma levels of cholesterol, however, differs from the one carried out by statins. While these drugs decrease the synthesis of endogenous cholesterol, berberine increases the activity and the number of hepatic LDL receptors, facilitating the removal of 'bad cholesterol' from blood. The combination of berberine with statins may still produce an interesting synergistic effect, also for its ability to inhibit a protein (PCSK9) responsible for the partial degradation of LDL receptors in the liver (which tend to promote statins).

More recently, new studies have highlighted the hypoglycemic effect of Berberine in patients with diabetes mellitus type 2. Also in this sense, the substance seems to act primarily at the receptor, increasing the expression of receptors for the insulin, with increased sensitivity to this hormone, and reduction of insulin resistance.

According to the present invention, the above objects are achieved thanks to the solution mentioned specifically in the following claims. In relation to the invention, the claims are an integral part of technical teaching provided.

The invention is explained below in detail with non-exhaustive examples of realization of the functional food preparation of the invention.

Example 1

For the purpose of stabilizing the levels of cholesterol and triglycerides has been effective the synergistic action of soy isoflavones associated with policosanol, including octacosanol, extracted from *Saccharum officinarum,* statin plant monacolin K by *Monascus purpureus* extract, coenzyme Q10 and also extracted from soybean (*Glycine max*), which have been added to a dairy product, and exactly yogurt, where out of 100 grams in total weight of the preparation there are:

*Saccharum officinarum* (drums—titled 60% in octacosanol) 35 mg
*Monascus purpureus* (yeast *Monascus* fermented substrate *Purpureus Oryza sativa* titled 1.5% in monacolin) 200 mg
*Glycine max* (beans titled 40% in isoflavones) 70 mg
Dairy Product semifluid—especially yogurt—to reach 100 g in total.

where the *Saccharum officinarum* and fermented red rice are added to the milk after 20 minutes of cooling following the pasteurization process and the *Glycine max* is added to the milk after 30 minutes of cooling in a multi-purpose apparatus commonly known in the dairy sector.

In this example, *Saccharum officinarum* brings the amount of daily recommended policosanol (Octacosanol), the *Oryza sativa* brings statin monacolin K and *Glycine max* provides isoflavones and coenzyme Q10. In addition to achieving optimal doses of policosanol, isoflavones and plant statins, coenzyme Q10 is used to cover the deficit of CoQ10 caused by intake of inhibitors of HMG-CoA reductase inhibitors used as cholesterol reducing drug, such as the above mentioned statins.

Example 2

A second example of implementation of the invention has been developed and defined in view of individual metabolic exceptions, which can offer a different and significant cholesterol-lowering response to food intake in which there is the association of soy isoflavones associated with policosanol, including octacosanol, plant statins extracts from *Medicago sativa,* the cynarin extracted from *Cynara scolimus,* and coenzyme Q10 extracted from soybean (*Glycine max*), which are added to a dairy product, and exactly yogurt, where on 100 grams in total weight of the preparation there are:
*Medicago sativa* (dried extract) 50 mg
*Cynara scolimus* (purified dry extract titled 5% in cynarin) 10 g
*Glycine max* (beans—titled 40% in isoflavones) 50 mg
*Monascus purpureus* (yeast of *Monascus Purpureus* fermented on a substrate of *Oryza sativa* titled 1.5% in monacolin) 200 mg
Dairy Product semifluid—exactly yogurt—to reach 100 g in total,
where the above mentioned substances are added to the milk after 30 minutes of cooling following the pasteurization process by making use of multi-purpose apparatus.

In this example, policosanol are contained in *Medicago sativa,* monacolin K is contained in *Oryza sativa,* while isoflavones and coenzyme Q10 are contained in *Glycine max.* Moreover, thanks to its significant content in folic acid, or acid pteroll (mono) glutamic acid or vitamin B9, the *Medicago sativa* exerts a containment of homocysteine. The main contribution of *Cynara scolimus* is in cynarin that, in addition to cholesterol-lowering action also plays an important action to protect the liver.

Example 3

In a third example of realization of a food preparation according to the invention the synergistic action of policosanol, isoflavones, plant statins and coenzyme Q10 are combined with the actions of Resveratrol and Berberine. In this example of realization the above active ingredients are added in the form of dry extracts of specific plant varieties to a rice based drink in which, out of 100 grams in total weight of the preparation are:
*Saccharum officinarum* (drums—titled 60% in octacosanol) 35 mg
*Berberis aristata* (dry extract 97% in berberine) 500 mg
*Glycine max* (beans titled 40% in isoflavones) 50 mg
*Monascus purpureus* (yeast *Monascus Purpureus* fermented on a substrate of *Oryza sativa* titled 1.5% in monacolin) 200 mg
*Vitis vinifera* (seed dry extract titled 90% in Resveratrol) 500 mg
rice milk (rice grains soaked in water, with added enzymes, pressed and filtered) to reach 100 g in total
where the plant extracts listed above are added at the end of the process of production of the rice milk.

In this realization in addiction to policosanol, isoflavones, statins and coenzymes are Resveratrol and Berberine. While statins reduce the synthesis of endogenous cholesterol, berberine increases the activity and the number of hepatic LDL receptors, thus facilitating the removal of 'bad cholesterol' from blood. The results obtained show that the combination of berberine with statins may still produce an interesting synergistic effect, also for its ability to inhibit a protein (PCSK9) responsible for the partial degradation of LDL receptors in the liver (that statins tend to promote).

The preparation of the invention is preferably a dairy product based on milk that has undergone at least a pasteurization or equivalent.

For semi-liquid dairy product means a product which has a viscosity (at 10° C.) less than 10.000 mPa*s.

Alternatively, the food preparation of the invention can be a soy drink or a rice drink.

Information and definitions relating to substances used in the preparation examples described above are shown below.
*Saccharum officinarum* (sugar cane):
contains policosanol, octacosanol in particular
0.5% protein content
0.2% fat
95% carbohydrates
0.005% iron
*Monascus purpureus* (yeast red rice) (yeast *Monascus Purpureus* fermented on a substrate of *Oryza sativa* titled 1.5% in monacolin):
1.5% monacolin
5% Policosanols
2.5% Astaxanthin
2.5% Coenzyme Q10
0.1% Folic acid
0.001% Vitamin B12
8.8% protein content
2.75% fat
60% carbohydrates
1.04% fibers
2.21% ash
21% amidoiso
*Glycine max* (soybean):
contains isoflavones, coenzyme Q10
13.09% protein content
6.7% fat
9.7% carbohydrate
1.1% fiber
69% water
1.59% ash
0.484% potassium
0.174% phosphorus
*Medicago sativa* (lucerne):
contains isoflavones, policosanol, saponins, coumarins, folic acid
26% protein content
0.2% fat
61% polysaccharides
23.7% fiber
4.9% starch
12.3% lignin
9.3% ash
37.9% nitrogen free extract
*Cynara scolimus* (artichoke)
contains cynarin, folic acid, Sylmarin, vitamin C
2.7% protein content
0.2% fat
2.5% carbohydrate
1.1% fiber
84% water The dairy products used in the context of the invention are milk, yogurt, butter, fresh cheese, mozzarella, crescenza cheese, ricotta cheese, cottage cheese, quark, mascarpone cheese, single-portion fresh cheese, via and matured cheeses.

The milk used in the production of the above dairy products may be of a variety of types, and can be chosen from cow's milk or sheep's or goat's milk or buffalo milk or mixtures thereof, or it could also be a milk plant as soy milk or rice milk.

The milk itself, when it comes from animal milk, preferably has undergone a process of pasteurization, sterilization or other heat treatment.

Preferably, yogurt means cow's milk fermented with *Lactobacillus bulgaricus* and *Streptococcus thermophilus*, where these organisms are alive and vital to the moment of consumption. The cell density must be equal to or greater than 100,000,000 cells per milliliter. The enzymes can also be probiotic, such as bifidobacteria and *lactobacilli acidophilus*. However, the yogurt may also be obtained from plant milk such as the soy milk.

The form of coenzyme Q10 that is used in the invention is extracted from the oil of *Glycine max* (soybean) with the Soxhlet method, a known technique.

BIBLIOGRAPHY

Arruzazabala M. L. et al. (2002). Antiplatelet effects of policosanol (20 and 40 mg/day) in healthy volunteers and dyslipidaemic patients. Clin Exp Pharmacol Physiol. 29(10), 891-7.

Bianchi A. (2005). Extracts of *Monascus purpureus* beyond statins—profile of efficacy and safety of the use of extracts of *Monascus purpureus*. Chines Journal Integr. Med. 11, 309-313.

Bitto A. (2010). Effettl estrogeni degll Isoflavoni—Dipartimento clinico sperimentale di Medicina e Farmacologia—Università degll Studl di Messina.

Castano, G., Mas, R., Fernandez, J. C. et al. (2001). "Effects of policosanol in older patients with type II hypercholesterolemia and high coronary risk" . J. Gerontol. A Biol. Sci. Med. Sci. 56, 186-92.

Castano G. et al (2003). Comparison of the effects of policosanol and atorvastatin on lipid profile and platelet aggregation in patients with dyslipidaemia and type 2 diabetes mellitus. Clin. Drud Investig.

Dallner G., Stocker R. (2005). Coenzyme Q10. Encyclopedia of dietary supplements.

Fintelmann V. (1996). Antidyspeptic and lipid lowering effects of artichoke (*Cynara scolymus*) extract. Results of clinical studies on efficacy and tolerability of Hepar S. L. registered trade mark forte on 553 patients. Z. Allg. Med. 72, 48-57.

Gebhardt R. (1997). Antioxidative and protective properties of extracts from leaves of the artichoke (*Cynara scolymus* L.) against hydroperoxide-induced oxidative stress in cultured hepatocytes. Toxicol. Appl. Pharmacol. 144, 279-286.

Gouni-Berthold I. et al. (2002). Policosanol: clinical pharmacology and therapeutic significance of a new lipid-lowering agent. Am Heart J. 143(2), 356-65.

Linnane A. W., Kopsidas G., Zhang C., Yarovaya N., Kovalenko S., Papakostopoulos P., Eastwood H., Graves S., Richardson M. (2002). Cellular redox activity of coenzyme Q10: effect of CoQ10 supplementation on human skeletal muscle. Free Radio Res. 36(4), 445-53.

Littaru G. P. & Tiano L. (2005). Clinical aspects of coenzyme Q10:un update. Curr. Opin. Clin. Nutr. Metab.

Mas R. et al. (1998). Effect of policosanol on platelet aggregation in type II hypercholesterolemia patients. Int. J. Tissue React.

Mas R. et al. (1999). Effects of policosanol in patients with type II hypercholesterolemia and additional coronary risk factors. Clin Pharmacol Ther. 65(4), 439-47.

Mizuno M., Quistorff B., Theorell H., Theorell M., Chance B. (1997). Effects of oral supplementation of coenzyme Q10 on 31P-NMR detected skeletal muscle energy metabolism in middle-aged post-polio subjects and normal volunteers. Mol Aspects Med. 18, 291-8.

Mosca G. (2008). Tesi dl laurea "Isoflavonl e proteine della sola"—Università degli Studi di Padova.

Niklowitz P., Menke T., Wiesel T., Mayatepek E., Zschocke J., Okun J. G., Andler W. (2002). Coenzyme Q10 in plasma and erythrocytes: comparison of antioxidant levels in healthy probands after oral supplementation and in patients suffering from sickle cell anemia. Clin Chim Acta. 326(1-2), 155-61.

Ortensi, G., Gladstein, J., Valil H. et al. (1997). A comparative study of policosanol versus simvastatin in elderly patients with hypercholesterolemia. Curr. Ther. Res. 58, 390-401.

Prat H. et al. (1999). Comparative effects of policosanol and two HMG-CoA reductase inhibitors on type II hypercholesterolemia. Rev Med Chil. 127(3), 286-94.

Tikkanen M. J. & Adlercreutz H. (2010). Ruolo degli Isoflavonoldl della sola nella prevenzione della malattla cardiovascolare—Dipartimento di Medicina—Ospedale Centrale dell'Università di Helsinki, Finlandia. Pubblicato su Biochem Pharmacol.

Valente M. (2009). I beneficl del Fltoestrogeni—Ginecologia e endocrinologia—Università la Saplenza.

Volpe R. (2008). Fltosteroli, riso rosso fermentato, policosanoli e tè verde riducono il colesterolo—CNR Roma—Nutrition, Metabolism and Cardiovascular Diseases.

Wegener T. et al. (1999). Pharmacological properties and therapeutic profile of artichoke (*Cynara scolymus* L). Wien Med. Wochenschr. 149, 241-7.

Zhan S. et al. (2005). Valutazione degli studl clinici esistenti sugli effettl della sola contenente isoflavoni sul colesterolo e sui trigliceridi di donne in menopausa. Am J Clin Nutr. 81(2), 397-408.

Zhuo X. G. et al. (2004). Soy isoflavone intake lowers serum LDL cholesterol: a meta-analysis of 8 randomized controlled trials in humans. J Nutr. 134(9), 2395-400.

The invention claimed is:

1. A functional food preparation to maintain cholesterol and triglycerides in a desired range in a human body and to reduce free radicals in a human body, to protect the arteries and cardiovascular system of a human body;
   said functional food is made of at least a milk/dairy product to which is added a mixture of botanical products, said mixture contains:
   a) polycosanols,
   b) isoflavones,
   c) plant statins,
   d) coenzymes and
   e) cynarin;
   wherein said polycosanols are present in the range of 0.005% to 0.06% by weight of the preparation; and wherein polycosanol's main molecules are octacosanol, tetracosanol and esacosanol, and wherein said polycosanol syntetic production comprises the extraction process of octacosanol conducted by cold pressing without using solvents to maximize its vitamin E content and its antioxidant factor;
   wherein said botanical products are present in the range of 0.005% to 0.1% by weight of the preparation;

wherein said isoflavones are present in the range of 0.005% to 0.1% by weight of the preparation; wherein said isoflavones, extracted from natural soy, can be found in the form of glucosinolate, while the bio-active form is the glucose-free isoflavone, which is the aglycone; said isoflavones must be activated through hydrolysis of its glucosidic group to acquire its biological function;

wherein said plant statins include monacolins, wherein said monacolins are present in the range of 0.01% to 0.1% by weight of the preparation and are extracted by fermentation of red rice with the addition of *Monascus purpureus*, and wherein said cynarin is present in the range of 1% to 20% by weight of the preparation and wherein said cynarin is not naturally present in the *Cynara scolimus* plant during the complete phenological cycle, but it is formed during a drying process; and wherein said at least one milk/dairy product is a member selected from the group consisting of: soy milk, rice milk, yogurt, butter, fresh cheese, mozzarella, crescenza cheese, ricotta cheese, cottage cheese, quark, mascarpone cheese, mild cream cheese, single-portion fresh cheese, and matured cheese.

2. The functional food preparation according to claim 1 wherein said mixture further comprises saponins, coumarins, and folic acid.

3. The functional food preparation according to claim 1 further comprising *Saccharum officinarum* containing 60% in octacosanol, extracted by cold pressing, without the use of solvents.

4. The functional food preparation according to claim 1, further comprising *Glycine max* beans containing 40% in isoflavones.

5. The functional food preparation according to claim 1, further comprising *Monascus purpureus* fermented on a substrate of *Oryza sativa* containing 1.5% in monacolin.

6. The functional food preparation according to claim 1 wherein said coenzymes are coenzyme Q10 extracted from the oil of *Glycine max* using the Soxhlet method.

7. The functional food preparation according to claim 1, further comprising a dry extract of *Medicago sativa*, present in the range of 0.005% to 0.06% by weight of the preparation.

8. The functional food preparation according to claim 1, further comprising a dry extract of *Cynara scolimus* containing at least 0.5% of cynarin, wherein said dry extract of *Cynara scolimus* is present in the range of 0.1% to 10% by weight of the preparation.

9. The functional food preparation according to claim 1 wherein said milk/dairy product is a soy milk based drink.

10. The functional food preparation according to claim 1 wherein said milk/dairy product is a rice milk based drink.

11. The functional food preparation according to claim 1 wherein said mixture further comprises Berberin, wherein said Berberin is present in the range of 0.1% to 2% by weight of the preparation.

12. The functional food preparation according to claim 1 wherein said mixture further comprises Resveratrol, wherein said Resveratrol is present in the range of 0.1% to 2% by weight of the preparation.

* * * * *